United States Patent
Schleich

(10) Patent No.: US 8,417,348 B2
(45) Date of Patent: Apr. 9, 2013

(54) PULSATILE COCHLEAR IMPLANT STIMULATION STRATEGY

(75) Inventor: Peter Schleich, Igls (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 803 days.

(21) Appl. No.: 12/267,858

(22) Filed: Nov. 10, 2008

(65) Prior Publication Data
US 2009/0125082 A1 May 14, 2009

Related U.S. Application Data

(60) Provisional application No. 60/986,690, filed on Nov. 9, 2007.

(51) Int. Cl.
*A61N 1/36* (2006.01)
*A61N 1/18* (2006.01)
*A61F 11/04* (2006.01)

(52) U.S. Cl. ............... 607/57; 607/55; 607/56

(58) Field of Classification Search ......... 607/55–57
See application file for complete search history.

(56) References Cited

U.S. PATENT DOCUMENTS

| | | | |
|---|---|---|---|
| 4,284,856 A | 8/1981 | Hochmair et al. | 179/107 E |
| 4,428,377 A | 1/1984 | Zollner et al. | 128/419 |
| 4,515,158 A | 5/1985 | Patrick et al. | 128/419 R |
| 5,215,085 A | 6/1993 | Von Wallenberg-Pachaly | 128/420.6 |
| 5,601,617 A | 2/1997 | Loeb et al. | 607/56 |
| 5,938,691 A | 8/1999 | Schulman et al. | 607/57 |
| 6,175,767 B1 | 1/2001 | Doyle, Sr. | 607/57 |
| 6,219,580 B1 | 4/2001 | Faltys et al. | 607/57 |
| 6,289,247 B1 | 9/2001 | Faltys et al. | 607/57 |
| 6,295,472 B1 | 9/2001 | Rubinstein et al. | 607/55 |
| 6,594,525 B1 | 7/2003 | Zierhofer | 607/57 |
| 6,600,955 B1 | 7/2003 | Zierhofer | 607/57 |

(Continued)

FOREIGN PATENT DOCUMENTS

| | | |
|---|---|---|
| WO | WO 99/35882 | 7/1999 |
| WO | WO 99/49815 | 10/1999 |

(Continued)

OTHER PUBLICATIONS

Grayden, et al, "A Cochlear Implant Speech Processing Strategy Based on an Auditory Model", *Proceedings of the 2004 Intelligent Sensors* Sensors Networks and Information Processing Conference, Dec. 14-17, 2004; pp. 491-496.

(Continued)

*Primary Examiner* — Carl H Layno
*Assistant Examiner* — Jon-Eric Morales
(74) *Attorney, Agent, or Firm* — Sunstein Kann Murphy & Timbers LLP

(57) ABSTRACT

An implantable device includes a multi-channel electrode array in which each channel is associated with an electrode in the array. An audio processing stage processes an input audio signal to produce output channel signals representing associated bands of audio frequencies. A timing and envelope detector processes the output channel signals in a sequence of sampling intervals, including, for each sampling interval, determining for each output channel signal a set of pulse timing requests. A pulse selection amplitude definition stage determines for each set of requested pulse timings a set of output pulses at specified times and amplitudes selected from the set of requested pulse timings based on a pulse selection inhibition function.

22 Claims, 10 Drawing Sheets

U.S. PATENT DOCUMENTS

| | | | | |
|---|---|---|---|---|
| 7,039,466 | B1 * | 5/2006 | Harrison et al. | 607/56 |
| 7,130,694 | B1 * | 10/2006 | Voelkel | 607/55 |
| 7,209,789 | B2 | 4/2007 | Zierhofer | 607/57 |
| 2005/0107843 | A1 | 5/2005 | McDermott et al. | 607/57 |
| 2005/0203589 | A1 * | 9/2005 | Zierhofer | 607/57 |
| 2006/0052841 | A1 | 3/2006 | Daly et al. | 607/57 |
| 2006/0080087 | A1 | 4/2006 | Vandali et al. | 704/207 |
| 2006/0227986 | A1 | 10/2006 | Swanson et al. | 381/312 |
| 2006/0265061 | A1 | 11/2006 | Kwon et al. | 623/10 |
| 2007/0156202 | A1 | 7/2007 | Zierhofer | 607/57 |
| 2009/0125082 | A1 * | 5/2009 | Schleich | 607/57 |

FOREIGN PATENT DOCUMENTS

| | | |
|---|---|---|
| WO | WO 01/19135 | 3/2001 |
| WO | WO 01/19304 | 3/2001 |
| WO | WO 2006/119069 | 11/2006 |

OTHER PUBLICATIONS

Kral, A., et al, "Spatial resolution of cochlear implants: the electrical field and excitation of auditory afferents", *Hearing Research*, vol. 121 (1998, pp. 11-28.

Loizou, P.C., "Signal Processing for Cochlear Prosthesis: A Tutorial Review", *IEEE*, Jan. 1997, pp. 881-885; 0-7803-3694-1/97.

Loizou, P.C., "Signal-Processing Techniques for Cochlear Implants", *IEEE Engineering in Medicine and Biology*, May/Jun. 1999, pp. 34-46.

McKay, Colette, et al, "The effect of rate of stimulation on perception of spectral shape by cochlear implantees", *Journal of Acoustical Society of America*, AIP/Acoustical Society of America, Melville, NY, US, vol. 118; No. 1; Jan. 1, 2005, pp. 386-392; XP012073185; ISSN: 001-4966.

Seeker-Walker, H., et al, "Time-domain analysis of auditory-nerve-fiber firing rates", *J. Acoust. Soc. Am.* 88(3), pp. 1427-1436 (1990).

Sit., J., et al, "A Low-Power Asynchronous Interleaved Sampling Algorithm for Cochlear Implants that Endoes Enelope and Phase Information", *IEEE Trans Biomed Eng.*, Jan. 2007; 54(1), pp. 138-149.

Vandali, A., et al, "Pitch ranking ability of cochlear implant recipients: A comparison of sound-processing strategies", *Accoust Soc. Am.*, May 2005; 117(5); pp. 3126-3138.

Wilson, B.S., et al, "Comparative Studies of Speech Processing Strategies for Cochlear Implants", *Laryngoscope*, vol. 96, No. 10, pp. 1068-1077, Oct. 1988.

Wilson, B. S., et al, "Better speech recognition with cochlear implants", *Nature*, vol. 352, pp. 236-238, Jul. 18, 1991.

Wilson, B. S., et al, "Seventh Quarterly Progress Report; Speech Processors for Auditory Prostheses", *Center for Auditory Prosthesis Research*, pp. 1-69, 1994.

Wilson, B. S., et al, "Temporal Representations With Cochlear Implants", *The American Journal of Otology*, 18:530-534, 1997.

Ziese, M., et al, "Speech Understanding with the CIS and the n-of-m Strategy in the MED-EL COMBI 40+ System", *ORL*, 2000;62:321-329.

\* cited by examiner

PULSATILE COCHLEAR IMPLANT STIMULATION STRATEGY

This application claims priority from U.S. Provisional Patent Application 60/986,690, filed Nov. 9, 2007, which is incorporated herein by reference.

FIELD OF THE INVENTION

The present invention relates to implantable medical devices, and more specifically, to techniques for coding stimulation pulses in such devices.

BACKGROUND ART

Cochlear implants are implantable systems which can provide hearing to profoundly deaf or severely hearing impaired persons. Unlike conventional hearing aids which mechanically apply an amplified sound signal to the middle ear, a cochlear implant provides direct electrical stimulation to multiple implant electrodes that excite the acoustic nerve in the inner ear. Most current cochlear implant electric stimulation coding strategies represent a sound signal by splitting it into distinct frequency bands and extracting the envelope (i.e., energy) of each of these bands. These envelope representations of the acoustic signal are used to define the stimulation amplitude of each electrode.

One current approach, the Fine Structure Processing (FSP) coding strategy, commercially available in the Med-E1 OPUS 1 and OPUS 2 speech processors, analyzes the phase of the band pass signals and synchronizes the stimulation pulses with specific events in the phase of the corresponding electrode. In FSP coding, time events are defined using the zero crossings of the band pass signal where all system channels are stimulated sequentially in a predetermined order (a "stimulation frame"). The stimulation rate or grid respectively of each channel is generally defined by the sum of the pulse durations and the pauses between consecutive stimulation pulses. The frame rate (i.e. the repetition rate) of one stimulation frame equals the stimulation rate or grid of each channel, typically 1000-2000 Hz.

FSP coding uses Channel Specific Sampling Sequences (CSSS), described, for example, in U.S. Pat. No. 6,594,525 (incorporated herein by reference) to represent the temporal information in the band pass signal. After a zero crossing in the band pass signal, a specific CSSS is started at the assigned electrode. The temporal accuracy is determined by the grid that is equal to the frame rate in FSP coding. This accuracy allows for coding temporal fine structure information up to several hundred Hertz. The temporal accuracy of CSSS in FSP is mainly defined by the pulse durations, i.e. at high pulse duration the accuracy of CSSS is low and the maximum frequency coded temporally is low as well.

Higher temporal accuracy of stimulation pulses can be achieved in an temporal fine structure coding strategy using CSSS together with the use of selected channel stimulation groups, as described, for example, in U.S. Pat. No. 7,283,876 (incorporated herein by reference). Different types of channels are defined (e.g. CSSS channels and envelope channels) and certain channels have to be grouped. For example, all the CSSS channels are placed into one or more groups in which some of the groups are repeated more often during a given stimulation frame. And within a given group, one or more of the channels can be stimulated simultaneously. This results in a temporal grid of CSSS stimulation which is a multiple of the frame rate. Improved temporal accuracy of the CSSS allows coding of phase information (up to about 1000 Hz) based on a high temporal grid using short pulse durations. With high pulse durations, temporal accuracy and frame rate (i.e. the rate of high frequency envelope channels) are reduced again. Most feasible combinations of CSSS, selected groups, and simultaneous stimulation, will have some mismatch between average CSSS rates of the highest CSSS channel and neighboring envelope channels. In such temporal fine structure coding strategies, a certain number of requested stimulation pulses are deselected. The number of deselected stimulation pulses (mainly within CSSS channels) is higher with higher pulse durations, which might lead to a loss of temporal information.

The current literature describes three other approaches that provide some temporal fine structure information. Peak Derived Timing (PDT) was described in Vandali et al., *Pitch Ranking Ability Of Cochlear Implant Recipients: A Comparison Of Sound-Processing Strategies*, J Acoust Soc Am. May 2005; 117(5):3126-38 (incorporated herein by reference). The PDT coding was experimentally used in cochlear implant users and derived the timing of stimulation pulses from the positive peaks in the band pass signals. Timing of the pulses was managed by an arbitration scheme which delayed or advanced simultaneously requested stimulation pulses. No refractory behavior was implemented in this algorithm.

Asynchronous Interleaved Sampling (AIS) was described in Sit et al., *A Low-Power Asynchronous Interleaved Sampling Algorithm For Cochlear Implants That Encodes Envelope And Phase Information*, IEEE Trans Biomed. Eng. January 2007; 54(1): 138-49 (incorporated herein by reference). The AIS strategy used asynchronous extraction of time events from band pass signals, but lacked any handling of interleaved stimulation pulses, which are a necessary part of a usable cochlear implant sound coding strategy.

Spike-based Temporal Auditory Representation (STAR) strategy is based upon an auditory model as described, for example, in Grayden et al., *A Cochlear Implant Speech Processing Strategy Based On An Auditory Model*, Proceedings of the 2004 Intelligent Sensors, Sensor Networks and Information Processing Conference, 14-17 Dec. 2004: 491-496 (incorporated herein by reference). The STAR approach, somewhat like CSSS, extracted the pulse timing from the zero crossings of the band pass signals. In this strategy 'spike timing contentions' are resolved by systematically shifting stimulation pulses to different time instances around the zero crossing. No details about the algorithm are given. The average stimulation rate on high frequency channels is restricted, but no details about the mechanism are given in the publication.

SUMMARY OF THE INVENTION

An implantable device includes a multi-channel electrode array in which each channel is associated with an electrode in the array. An audio processing stage processes an input audio signal to produce output channel signals representing associated bands of audio frequencies. A timing and envelope detector processes the output channel signals in a sequence of sampling intervals, including, for each sampling interval, determining for each output channel signal: i. a set of requested pulse timings containing a plurality of pulse timing requests, and ii. a set of corresponding envelope signals representing pulse magnitude for pulse timing requests. A pulse selection amplitude definition stage determines for each set of requested pulse timings: i. a set of output pulses at specified times selected from the set of requested pulse timings based on a pulse selection inhibition function, and ii. a stimulation amplitude associated with each output pulse. The multi-channel electrode array applies the output pulses at their associated stimulation amplitudes to surrounding tissue.

In more specific embodiments, the inhibition function may be constant at times so as to define an absolute inhibition state, and/or may be changing at times so as to define a relative inhibition state. The inhibition function may be output channel dependent and/or pulse magnitude dependent, for example, reflecting a ratio of inhibition state to pulse magnitude. The output pulses may be selected based on length of an inhibition state defined by the inhibition function; for example, the output pulses may be selected preferentially based on shortness of the inhibition state.

In specific embodiments, the input audio signal includes temporal structure characteristics which are represented in the output channel signals by channel specific sampling sequences (CSSS) and/or are reflected in the specified times of the output pulses. The electrode array may specifically be a cochlear implant electrode array.

DETAILED DESCRIPTION OF SPECIFIC EMBODIMENTS

Embodiments of the present invention are directed to a signal coding strategy for an implantable device having a multi-channel electrode array. The signal coding strategy encodes temporal characteristics of sound signals at a higher temporal accuracy and higher pulse durations than previously. Temporal fine structure is encoded and stimulation of refractor nerve populations can be inhibited by an inhibition function that determines whether or not stimulation pulses are delivered to one or more electrodes. Such signal coding is no longer based upon fixed stimulation rates and channel orders, and the encoding of the temporal fine structure is more accurate, even at long pulse durations.

Figure 1:
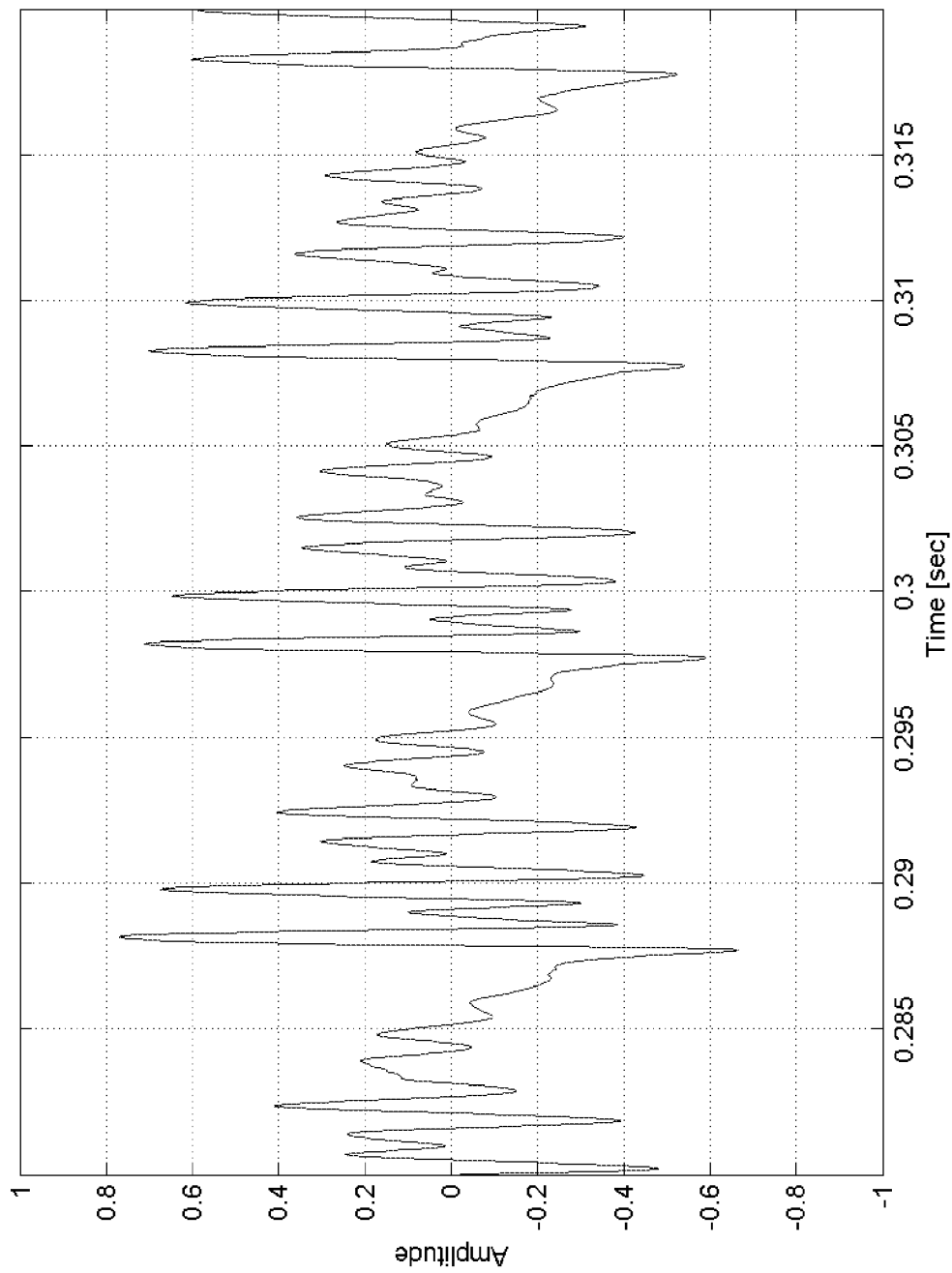
FIG. 1 shows an example of a typical acoustic signal.
Figure 2:
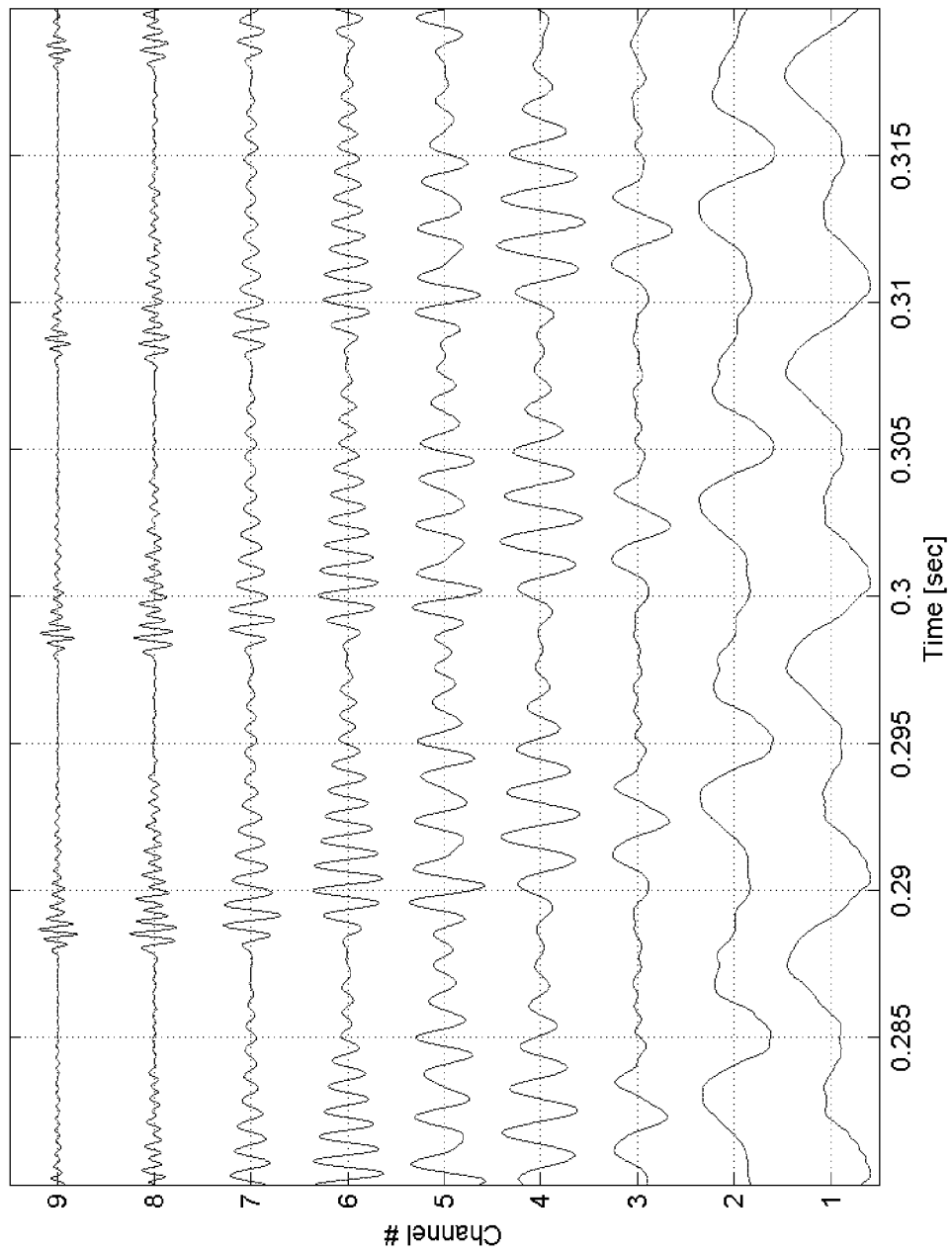
FIG. 2 shows an acoustic signal decomposed by band pass filtering by a bank of filters into a set of signals (input channels).

FIG. 1 shows a typical sound signal in which the overall amplitude varies over a short period of time. Such a sound signal inherently contains specific timing information that characterizes the signal. The sound signal in this form as an audio electrical signal is typically pre-processed into multiple output channel signals. For example, one common approach is to pre-process the initial audio signal with a bank of filters where it is decomposed by band pass filtering to form a set of output channel signals such as the example shown in FIG. 2, each of which represents an associated band of audio frequencies. Alternatively, in another embodiment, the initial audio signal can be processed by one or more non-linear filters which provide multiple output channel signals.

Figure 3:
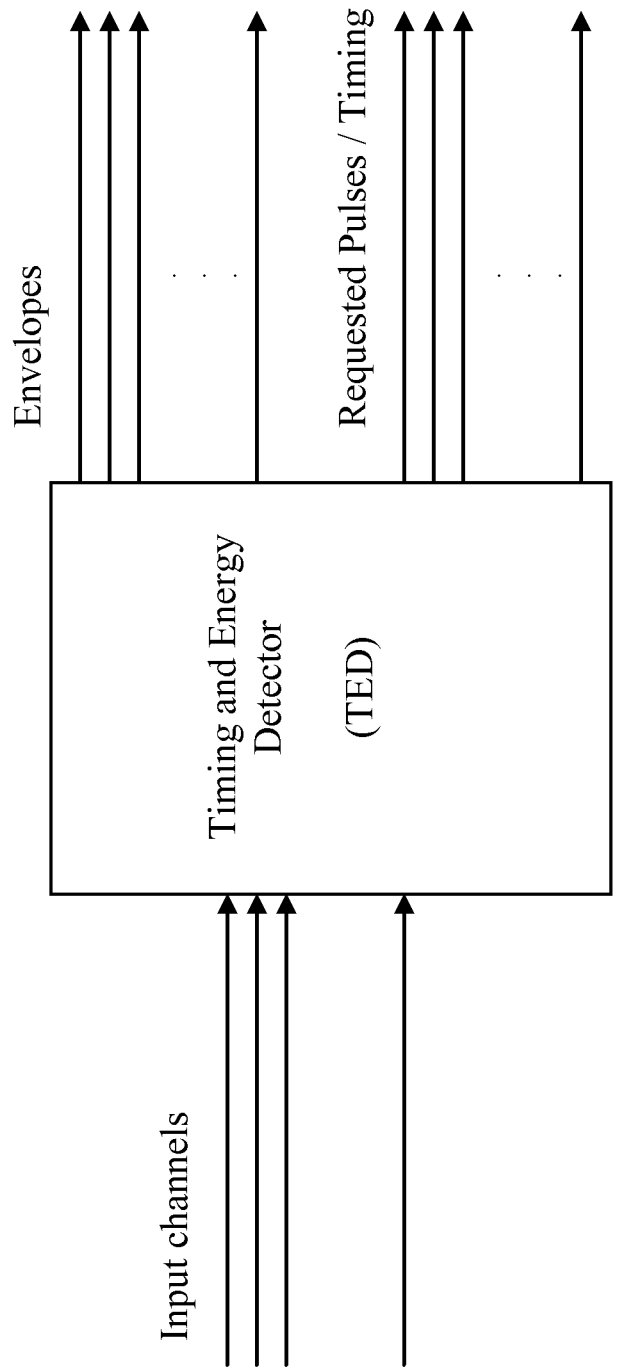
FIG. 3 shows an example of a Timing and Energy Detector according to an embodiment of the present invention.
Figure 4:
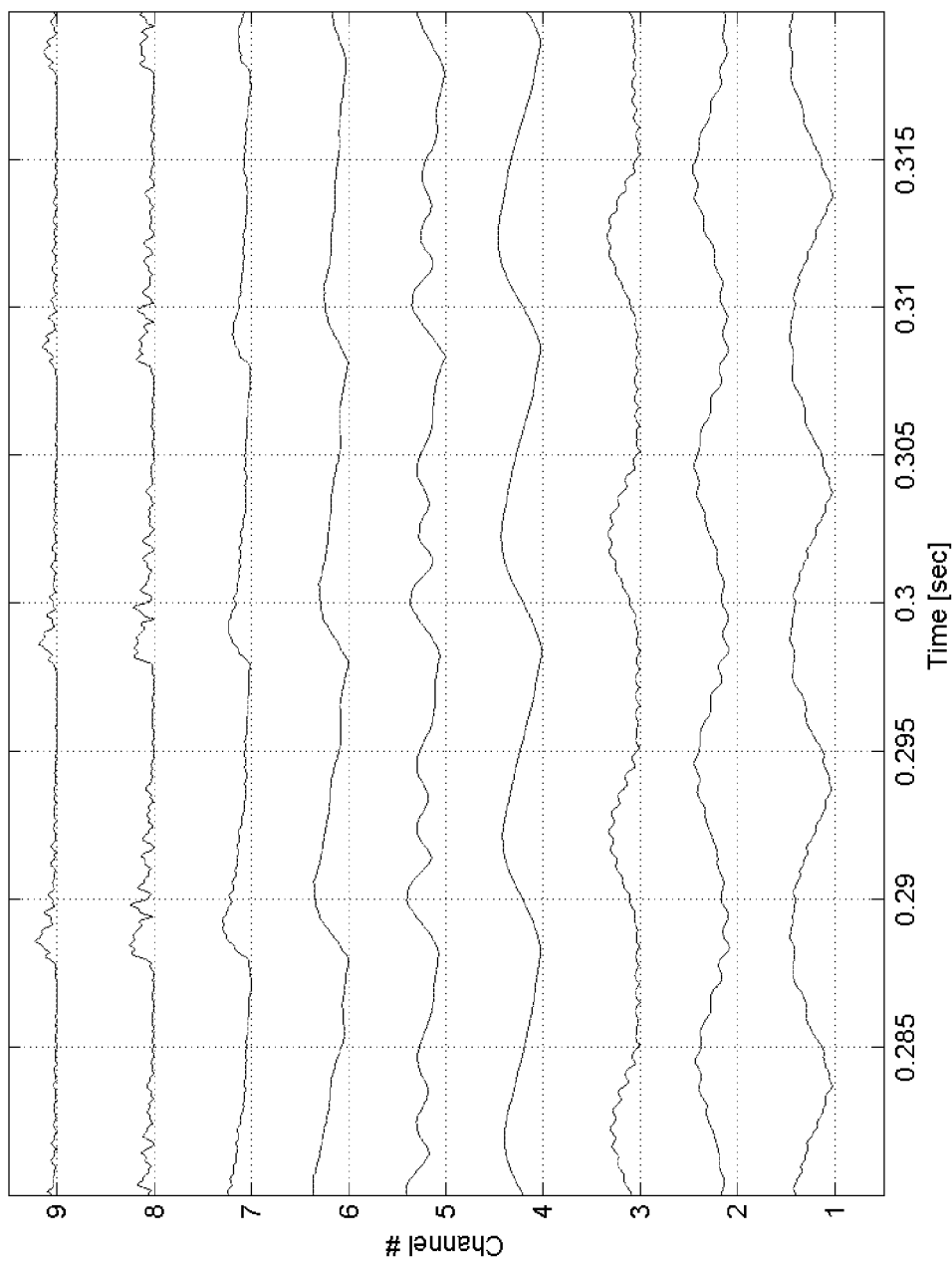
FIG. 4 shows examples of the envelopes extracted from the set of input signals.
Figure 5:
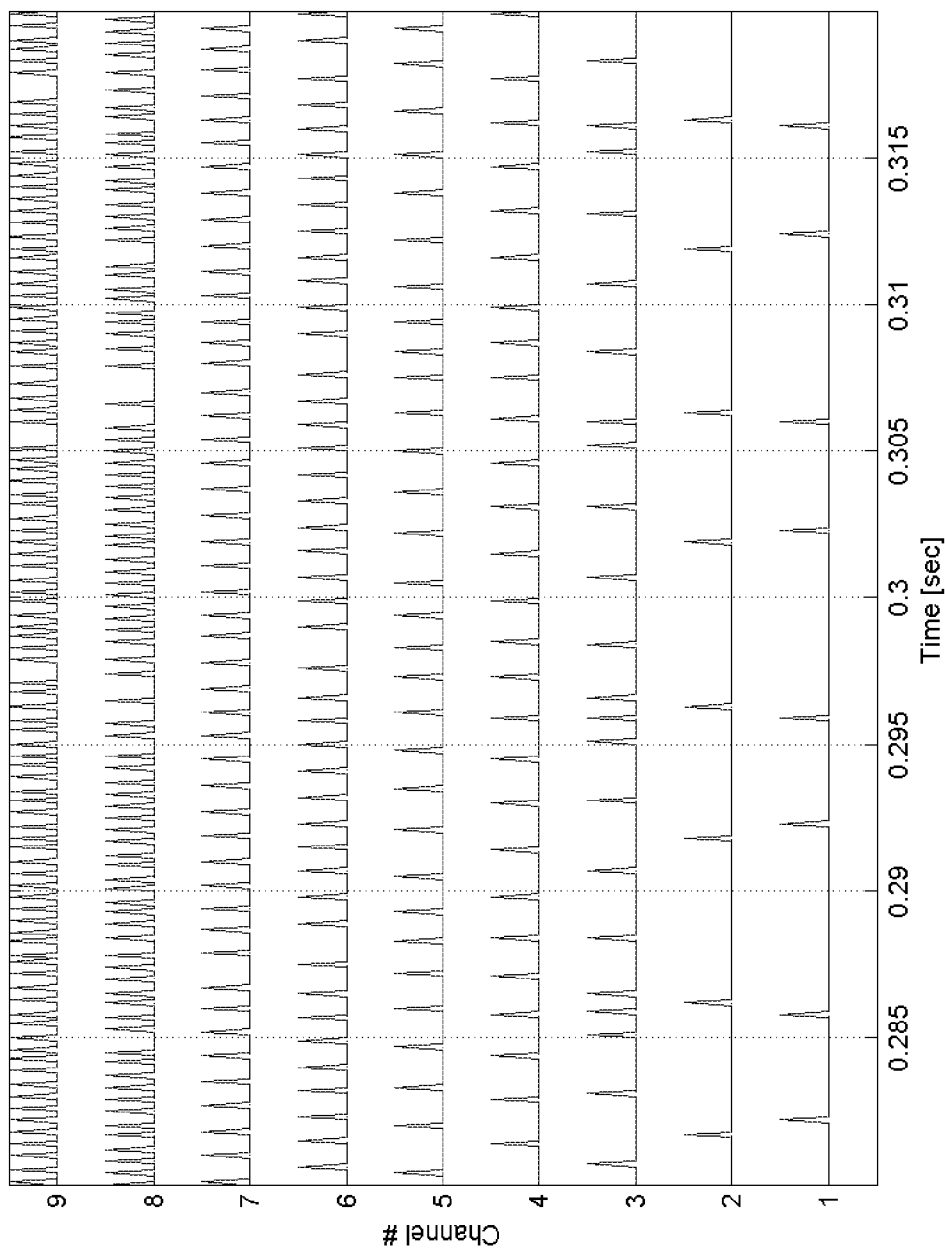
FIG. 5 shows timing of requested stimulation pulses extracted from the set of input signals.

Unlike prior fine structure processing approaches where different types of output channels have to be defined (e.g., CSSS fine structure channels and envelope channels), embodiments of the present invention treat all output channels equally. FIG. 3 shows an example of a Timing and Envelope Detector (TED) that receives as an input a set of output channel signals such as the sound signals shown in FIG. 2 from a bank of band pass filters. The TED processes these output channel signals in a continuing sequence of sampling intervals which are sampled at a given rate that, for example, may be defined by the pulse durations used for the electrical stimulation (e.g. the inverse of the maximum pulse duration). The TED extracts certain time events from each sampling interval, e.g., zero crossings, signal maxima, adaptive threshold levels, etc. as well as envelope information. The TED outputs a set of envelope signals (shown, for example, in FIG. 4) serving for the calculation of pulse magnitudes, and a set of time event signals (shown, for example, in FIG. 5) that flag requested stimulation pulses.

Figure 6:
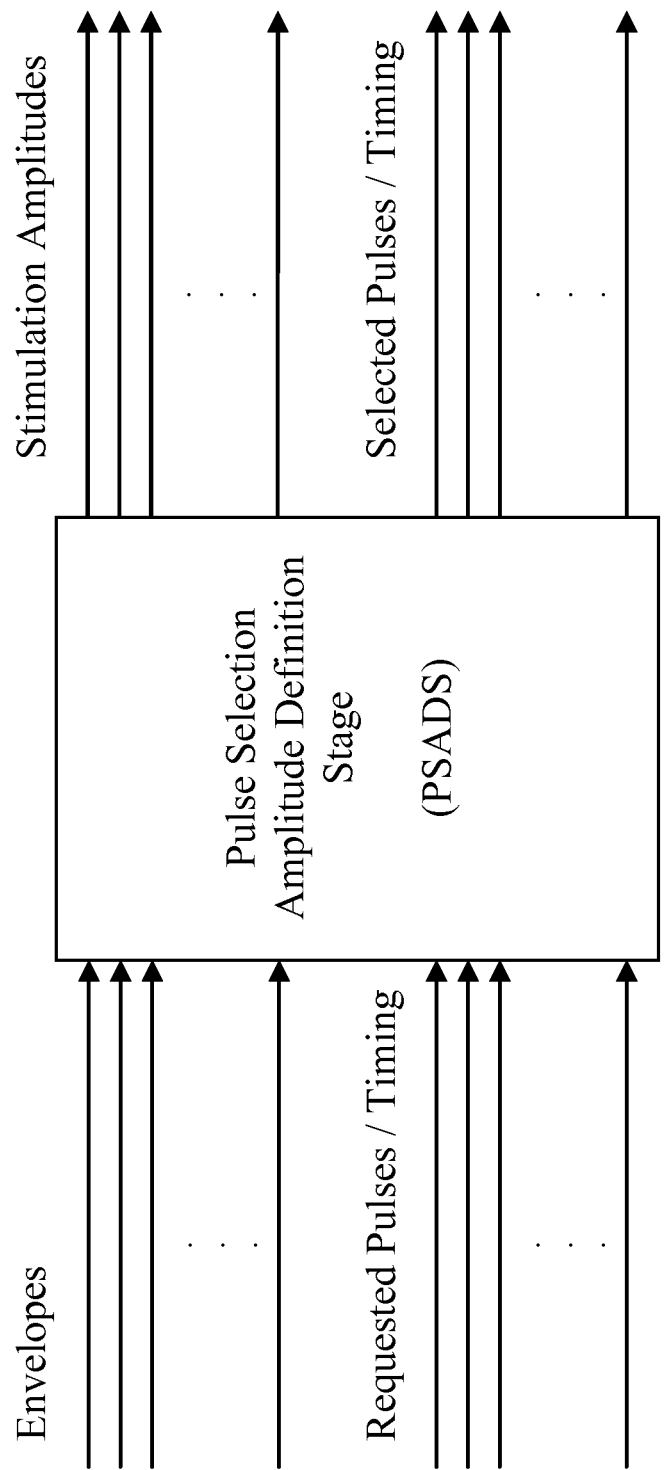
FIG. 6 shows an example of a Pulse Selection and Amplitude Definition Stage (PSADS) according to one embodiment of the present invention.
Figure 7:
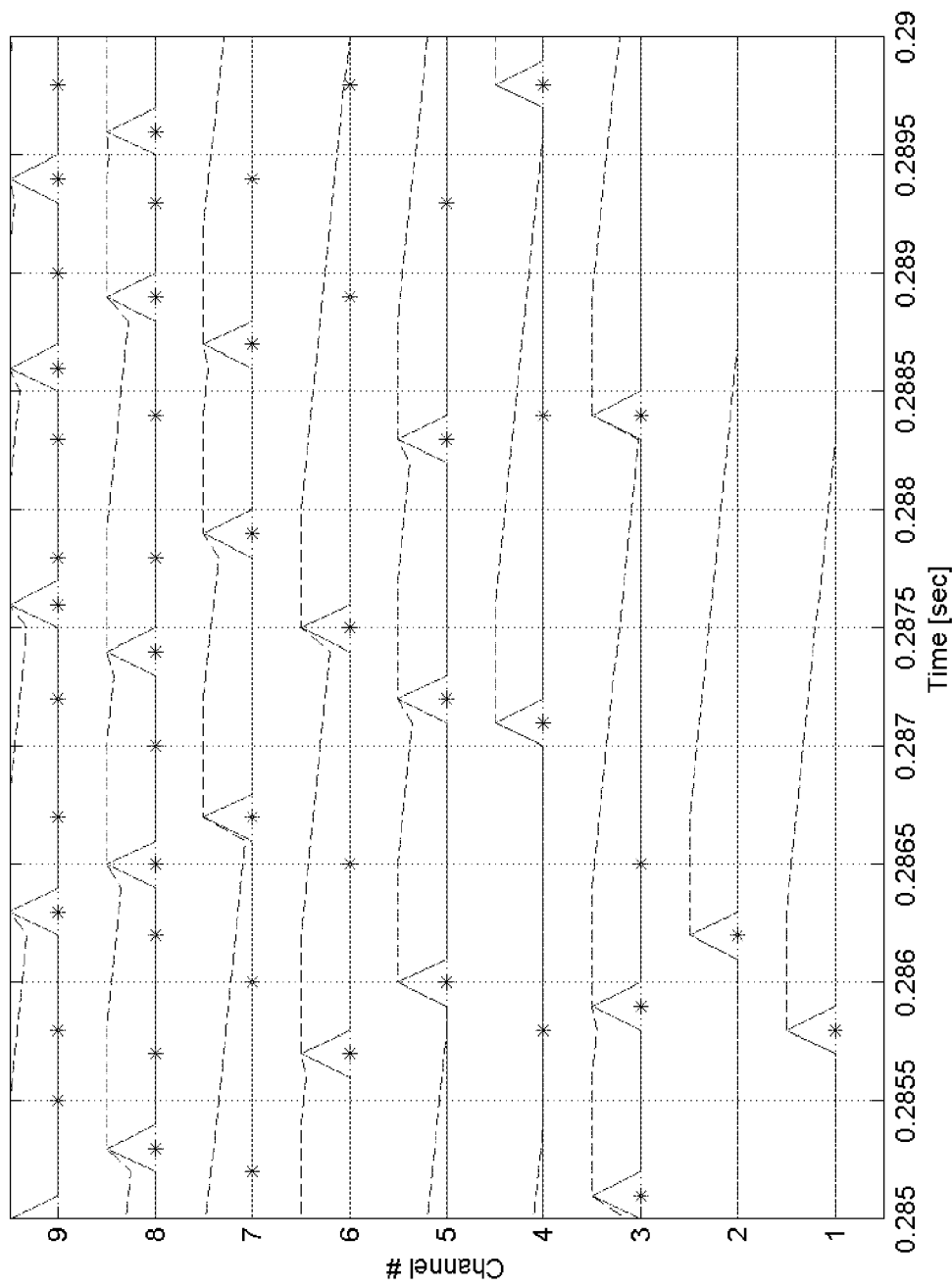
FIG. 7 shows an example of a possible implementation of a pulse selection algorithm within a PSADS.

As shown in FIG. 6, the TED outputs are provided to a Pulse Selection/Amplitude Definition Stage (PSADS) that selects a reduced set of time events (output stimulation pulses) and calculates stimulation amplitudes for the selected output pulses. The PSADS uses an inhibition function to calculate and analyze an inhibition state for each output channel. Within each sampling interval, the requested pulses are identified, and based on the inhibition states and envelopes of identified channels, at least one channel requesting a pulse is selected. For example, one way for the PSADS to select pulses might be to select one or more pulse requests within each sampling interval which have the shortest associated inhibition states. More complex selection algorithms can take into account the envelopes of the requested pulses so that the ratio of the inhibition state to the pulse amplitude serves as a selection criterion. FIG. 7 illustrates the selection process using a simple prototype of an inhibition function where the asterisks represent the timing of requested pulses per channel, solid lines depict the selected pulses, and dashed lines depict the inhibition states.

Figure 8:
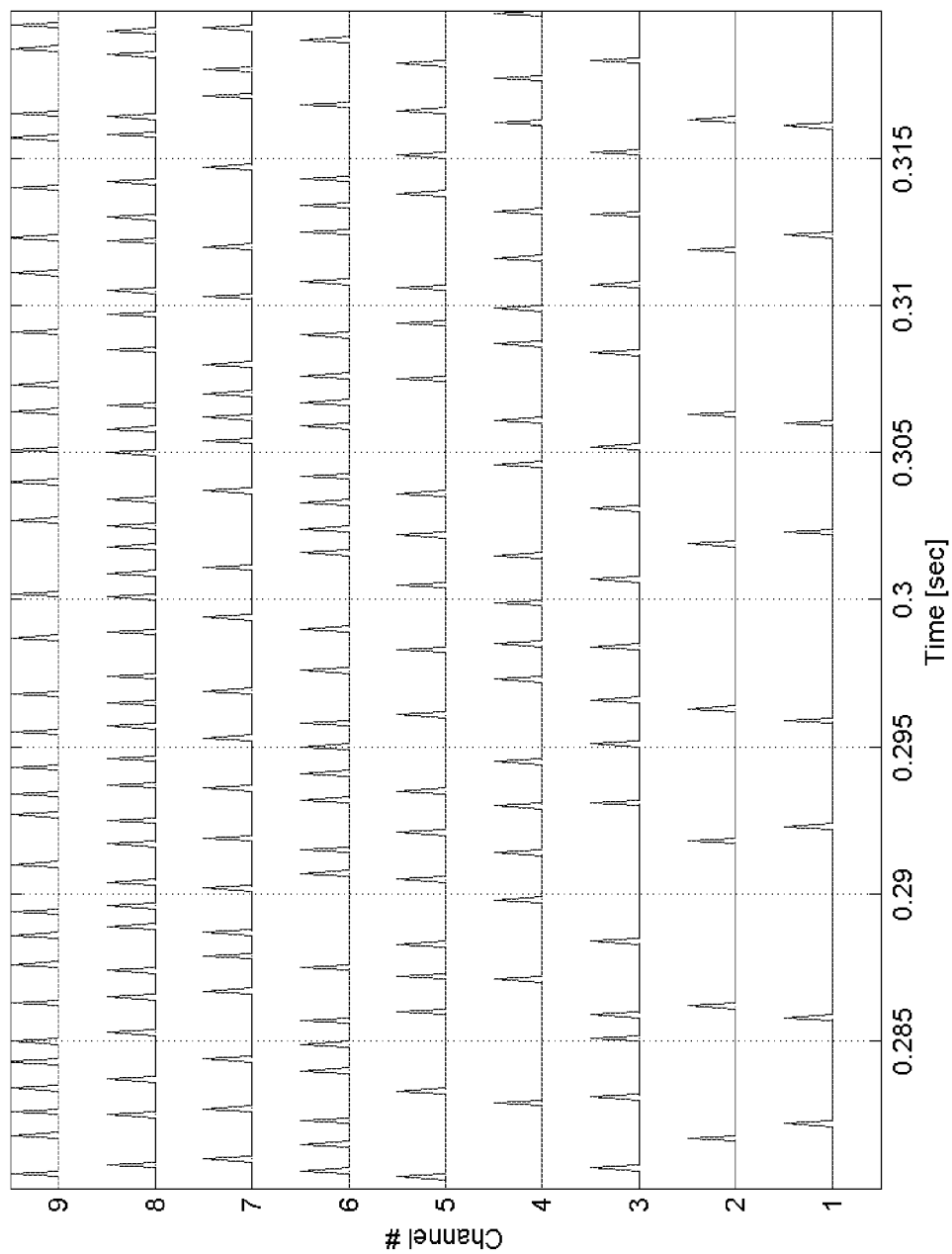
FIG. 8 shows an example of timing of the selected stimulation pulses according to an embodiment.
Figure 9:
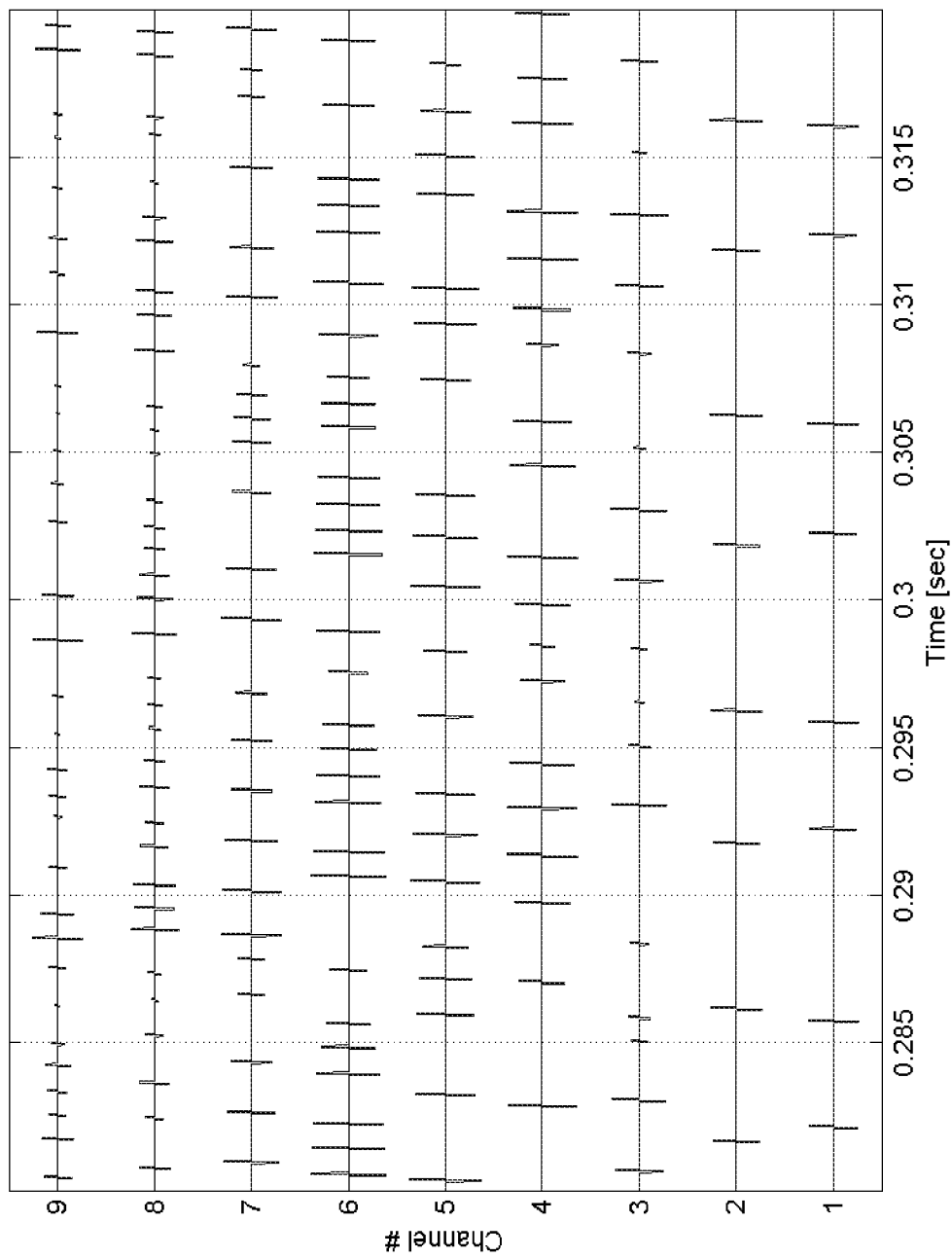
FIG. 9 shows an example of biphasic stimulation pulses in a sequential implementation of the system.
Figure 10:
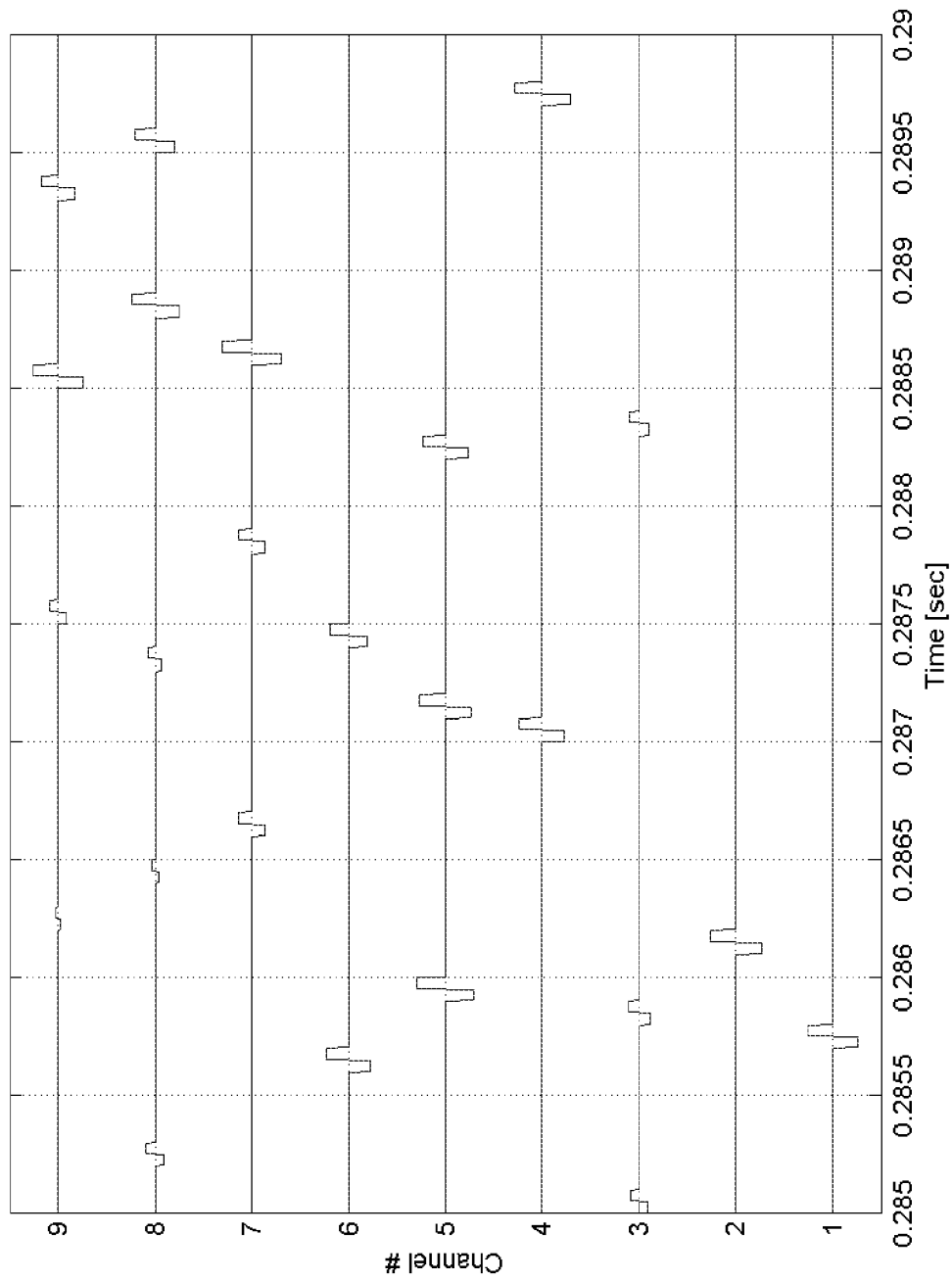
FIG. 10 shows further details of the biphasic stimulation pulses in a sequential implementation of the system.

Once a pulse request is selected as an output pulse, a channel- and amplitude-specific inhibition function is triggered on the selected output channel. In the specific embodiment shown in FIG. 7, the inhibition function is constant for some hundreds of microseconds (e.g., 500 µs) during a maximum or absolute inhibition phase, and then decreases towards zero over another period of several hundred microseconds (e.g., 1500 µs) which defines a relative inhibition phase. In this embodiment, requested pulses that occur within the absolute inhibition phase are not selected as output pulses for stimulation. Thus, in this example, inhibition times can be used to define the maximum channel-specific stimulation rate of the system. FIG. 8 illustrates the reduced set of time events (selected output pulses) resulting from this pulse selection. When compared to the initially requested pulse timings shown in FIG. 5, the number of selected output pulse timings produced by the PSADS, especially at higher frequencies, is markedly reduced. FIG. 9 shows the resulting biphasic stimulation pulses and their pulse amplitudes which are applied to the different channel electrodes. FIG. 10 shows a detailed expansion of a portion of the time illustrated in FIG. 9.

Such stimulation timing approaches can provide very accurate representation of low frequency temporal fine structure. For example, the time grid of stimulation per output channel can be defined by the maximum pulse duration required for electrical stimulation. With typical biphasic pulse durations of 50 μs, a time grid of up to 20 kHz may be realized. Even with relatively long electrical pulses, a higher timing accuracy of timing can be achieved. For example, with a 100 μs pulse duration on each output channel, a 10 kHz stimulation grid may be achievable. In an embodiment in which only one output pulse is selected for each sampling interval, the time grid is twice as fast as the fastest possible combination of just CSSS with selected electrode channel groups also applying one stimulation pulse at any time instance. Compared to the fastest possible combinations of CSSS with selected electrode channel groups, the number of deselected pulses can be largely reduced with specific embodiments. For example, at a time grid of 20 kHz and an absolute inhibition phase of 500 μs, a negligibly low number of requested stimulation pulses has to be deselected from output channels carrying a temporal fine structure of up to above 1000 Hz.

Specific embodiments can be implemented in a system with relatively low supply voltage such as a fully implantable cochlear implant system. In such a system, low compliance voltages would need relatively long stimulation pulses to achieve comfortable loudness. Embodiments enable presentation of temporal fine structure even at low supply voltages and can therefore be used in patients with low compliance voltages. A specific embodiment could be implemented with cochlear implants capable of either simultaneous stimulation or sequential stimulation.

Embodiments could also be useful for patients suffering from facial stimulation due to the cochlear implant stimulation. Such applications need relatively long pulse durations, and under such conditions, embodiments of the present invention are able to exactly transmit temporal fine structure.

The type and form of a channel-/amplitude-specific inhibition function can be used to define channel specific stimulation rates. The above described system with the above described prototype inhibition function with an absolute/maximum inhibition of 500 μs and the channel selection based exclusively on the inhibition function would allow 2000 Hz stimulation per channel at a maximum. Longer durations of absolute inhibition could be used to drastically reduce power consumption through electrical stimulation.

Some embodiments may also better mimic the natural neural behavior of the human ear. In particular, neural populations stimulated by electrodes connected to low frequency channels would be stimulated at lower rates. Stimulation on these electrodes will be relatively deterministic for a broad range of inhibition functions and times. High frequency channels can apply pseudo-stochastic timing to stimulation pulses. For a given TED and selection of inhibition time constants and pulse widths (time grid), the channel specific stimulation rate would be nearly equal to the characteristic frequency of the corresponding electrode channel, whereas for higher frequency electrode channels, a "natural" saturation of stimulation rate may be obtainable. The inhibition function may allow for the refractory behavior of stimulated nerve populations within an electrode channel, which would also lead to a reduction of stimulation power at a constant loudness percept.

Specific embodiments of the PSADS may well provide additional functionality useful for selecting and defining the output pulses. Accordingly, the PSADS may typically contain hardware and/or software modules to that end, such as non-linear circuitry for defining patient- and electrode-specific stimulation amplitudes. For example, specific implementations of an inhibition function algorithm may take into account such goals. As a result, in specific embodiments the PSADS could be more complex than as described above.

Embodiments of the invention may be implemented in any conventional computer programming language. For example, preferred embodiments may be implemented in a procedural programming language (e.g. "C") or an object oriented programming language (e.g., "C++", Python). Alternative embodiments of the invention may be implemented as pre-programmed hardware elements, other related components, or as a combination of hardware and software components.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of activating electrodes in an implanted multi-channel electrode array where each channel is associated with an electrode in the array, the method comprising:
   processing an input audio signal to produce a plurality of output channel signals each representing an associated band of audio frequencies;
   processing the output channel signals in a sequence of sampling intervals, wherein for each sampling interval, the processing includes:
   i. determining for each output channel signal:
      a) a set of requested pulse timings containing a plurality of pulse timing requests, and
      b) a set of corresponding envelope signals representing pulse magnitude for pulse timing requests; and
   ii. determining for each set of requested pulse timings:
      a) a set of output pulses at specified times selected from the set of requested pulse timings based on a pulse selection inhibition function configured to select a lower proportion of pulse timings corresponding to a band having a relatively high frequency than pulse timings corresponding to a band having a relatively low frequency, and
b) a stimulation amplitude associated with each output pulse; and activating electrodes in the array with corresponding output pulses at their associated stimulation amplitudes.

2. A method according to claim 1, wherein the inhibition function is constant at times so as to define an absolute inhibition state.

3. A method according to claim 1, wherein the inhibition function is changing at times so as to define a relative inhibition state.

4. A method according to claim 1, wherein the inhibition function is pulse magnitude dependent.

5. A method according to claim 4, wherein the inhibition function reflects a ratio of inhibition state to pulse magnitude.

6. A method according to claim 1, wherein the inhibition function is output channel dependent.

7. A method according to claim 1, wherein output pulses are selected based on length of an inhibition state defined by the inhibition function.

8. A method according to claim 7, wherein output pulses are selected preferentially based on shortness of the inhibition state.

9. A method according to claim 1, wherein the input audio signal includes temporal structure characteristics which are represented in the output channel signals by channel specific sampling sequences (CSSS).

10. A method according to claim 1, wherein the input audio signal includes temporal structure characteristics which are reflected in the specified times of the output pulses.

11. A method according to claim 1, wherein the electrode array is a cochlear implant electrode array.

12. An implantable device having a multi-channel electrode array, each electrode in the array being associated with a signal processing output channel, the device comprising:
an audio processing stage for processing an input audio signal to produce a plurality of output channel signals each representing an associated band of audio frequencies;
a timing and envelope detector for processing the output channel signals in a sequence of sampling intervals, wherein for each sampling interval, the processing includes determining for each output channel signal:
i. a set of requested pulse timings containing a plurality of pulse timing requests, and
ii. a set of corresponding envelope signals representing pulse magnitude for pulse timing requests;
a pulse selection amplitude definition stage for determining for each set of requested pulse timings:
i. a set of output pulses at specified times selected from the set of requested pulse timings based on a pulse selection inhibition function configured to select a lower proportion of pulse timings corresponding to a band having a relatively high frequency than pulse timings corresponding to a band having a relatively low frequency, and
ii. a stimulation amplitude associated with each output pulse; and
the multi-channel electrode array for applying the output pulses at their associated stimulation amplitudes to surrounding tissue.

13. An implantable device according to claim 12, wherein the inhibition function is constant at times so as to define an absolute inhibition state.

14. An implantable device according to claim 12, wherein the inhibition function is changing at times so as to define a relative inhibition state.

15. An implantable device according to claim 12, wherein the inhibition function is pulse magnitude dependent.

16. An implantable device according to claim 15, wherein the inhibition function reflects a ratio of inhibition state to pulse magnitude.

17. An implantable device according to claim 12, wherein the inhibition function is output channel dependent.

18. An implantable device according to claim 12, wherein output pulses are selected based on length of an inhibition state defined by the inhibition function.

19. An implantable device according to claim 18, wherein output pulses are selected preferentially based on shortness of the inhibition state.

20. An implantable device according to claim 12, wherein the input audio signal includes temporal structure characteristics which are represented in the output channel signals by channel specific sampling sequences (CSSS).

21. An implantable device according to claim 12, wherein the input audio signal includes temporal structure characteristics which are reflected in the specified times of the output pulses.

22. An implantable device according to claim 12, wherein the electrode array is a cochlear implant electrode array.

* * * * *